United States Patent [19]

Bruno et al.

[11] Patent Number: 4,713,064

[45] Date of Patent: Dec. 15, 1987

[54] ENTERAL FEEDING DEVICES

[75] Inventors: Robert Bruno, Avon; Stuart R. Kipperman, Easton; Geoffrey R. Mayer, Trumbull, all of Conn.; Michael Thomas, Ann, Ohio

[73] Assignee: Sherwood Medical Company, St. Louis, Mo.

[21] Appl. No.: 853,400

[22] Filed: Apr. 18, 1986

Related U.S. Application Data

[63] Continuation of Ser. No. 728,862, Apr. 30, 1985, abandoned.

[51] Int. Cl.[4] .............................................. A61M 5/85

[52] U.S. Cl. .................................... 604/257; 604/260; 215/10

[58] Field of Search ................. 604/257, 260, 403, 77, 604/270; D24/56; 215/10, DIG. 3; 206/503–510, 515

[56] References Cited

U.S. PATENT DOCUMENTS

| | | | |
|---|---|---|---|
| D. 247,309 | 2/1978 | Safianoff | D24/56 |
| 951,044 | 3/1910 | Axford | 604/257 |
| 3,323,668 | 6/1967 | Hills | 215/10 |
| 3,872,868 | 3/1975 | Kline | 604/403 |
| 3,880,311 | 4/1975 | McPhee | 604/260 |
| 3,926,341 | 12/1975 | Lhoest | 604/403 |
| 4,308,955 | 1/1982 | Schieser et al. | 215/10 |
| 4,513,865 | 4/1985 | Melzi et al. | 215/10 |

*Primary Examiner*—C. Fred Rosenbaum
*Assistant Examiner*—H. Macey
*Attorney, Agent, or Firm*—Stanley N. Garber; Andrew J. Beck; William R. O'Meara

[57] ABSTRACT

Enteral feeding devices for supplying liquid nourishment to a human patent. Each device having longitudinally extending projections and recesses adapted to mate or nest together so that a plurality of such containers can be placed in side-by-side or stacked relationship for efficient space-saving storage or shipment. The devices can be filled with liquid nourishment from either end. The container has a substantially flat end surface so that the container can be placed standing in an upside down position and a cap closing a spout will assist in positioning the container. There is a handle having a first position whereby the container can be placed on a hook adjacent the patient. The handle has a second out-of-the-way position permitting the container to be placed in the upside down position.

10 Claims, 5 Drawing Figures

ENTERAL FEEDING DEVICES

This is a continuation of co-pending application Ser. No. 728,862, filed Apr. 30, 1985, now abandoned.

FIELD OF INVENTION

This invention relates to enteral feeding devices and more particularly to new and improved enteral feeding devices that are particularly adapted to fit or nest together so that they can be conveniently stored in a side-by-side or stacked relationship in a filled or unfilled condition.

BACKGROUND OF THE PRIOR ART

There are in hospitals, nursing homes and other similar institutions a number of human patients who are incapable of taking nourishment in the conventional fashion. In some instances the patients are in this condition as a result of surgery or injury. In other instances, the patients are unable to take nourishment as a result of old age and/or senility.

In any event, it is sometimes necessary to provide means for providing such patients with nourishment. Typically, the patients are provided nourishment through the naso-gastric passages. In such event a naso-gastric tube is inserted into the patient through the naso-gastric passages. The naso-gastric tube is connected to and communicates with a container or the like which contains nourishment in a liquid form which will be fed to the patient by gravity or pump. The contents of the liquid nourishment may vary from patient to patient depending on the condition and needs of the patient. Thus, while in some instances a standardized liquid formulation may be used, in other instances a special formulation may be desired. Where a standard commercially available formulation is used the feeding container can be filled or replenished at the patient's bedside. On the other hand, where a special formulation is required, it can be mixed or formulated in the kitchen or formulary and placed within the container at that time and then transported to the patient.

In accordance with prior practices numerous types of feeding containers can be used. In one type of prior art practice a flexible bag-like container is employed. While such flexible bag-like containers are satisfactory in many instances they do not provide accurate readings on the amount of liquid nourishment within the bag due to its flexibility. Such bag-like feeding containers can be difficult to store in a space saving manner since the shape is not necessarily consistent with efficient space-saving storage. There is also the possibility of leakage during or after storage.

In other prior art practices rigid members are used as feeding containers. The problem with such prior rigid containers is that they lack versatility and are difficult to stack in large numbers for transport to the place of use such as a hospital or nursing home.

OBJECTS OF THE INVENTION

It is an object of this invention to provide a new and improved rigid enteral feeding device made of polyethylene or some other plastic rigid material.

It is another object of this invention to provide a new and improved enteral feeding device wherein the containers can be nested in side-by-side relationship for convenient and efficient storing or transport.

A still further object of this invention is to provide a new and improved enteral feeding device which can be filled adjacent to the patient or at another location while standing in a vertical position.

A further object of this invention is to provide a new and improved enteral feeding container wherein the feeding container has openings at each end for supplying the container with liquid nourishment while in either upright or upside down position.

Another object of this invention is to provide a new and improved rigid enteral feeding container wherein the container can be vertically positioned on one end for supplying liquid nourishment to the container.

A further object of this invention is to provide a new and improved rigid enteral container having cooperating projections and recesses so that the containers can be nested tobether in side-by-side or stacked relasionship for efficient space saving storage and/or transport.

An added object of this invention is to provide more accurate readings on the amount of liquid by virtue of a more rigid structure.

Additional objects and ádvantages of the invention will be set forth in the description which follows and, in part, will be obvious from the description; the objects and advantages being realized and attained by means of the instrumentaion, parts, apparatus, steps and procedures particularly pointed out in the appended claims.

BRIEF DESCRIPTION OF THE INVENTION

Briefly described, the present invention relates to new and improved rigid enteral feeding containers. the rigid enteral feeding container has openings at both ends permitting the container to be filled with liquid nourishment at the patient's bedside or at a remote location. The enteral container is constructed so that it can be placed upright with the assistance of the cap on a flat surface for insertion of a formulated liquid nourishment.

The rigid enteral container of this invention has a generally rectangular shape wherein one side has a projection extending substantially along its length and the other side has a recess extending along its length. The projection and recess are dimensioned so that the projection mates within the recess on another container to provide for efficient space saving storage of numerous devices. For convenience in use, the rigid enteral feeding container is provided with a hinged handle adapted for use with a hook or the like so that the containers can be hung adjacent the patient for gravity feeding of the patient.

The hinged handle can be pivoted to an out-of-the-way position so that the enteral containers can be efficiently placed in end-to-end relationship.

The invention consists of the novel parts, constructions and improvements shown and described.

The accompanying drawings which are incorporated in and constitute a part of this specification illustrate an embodiment of the invention and together with the description, serve to explain the principles of the drawings.

Figure 1:
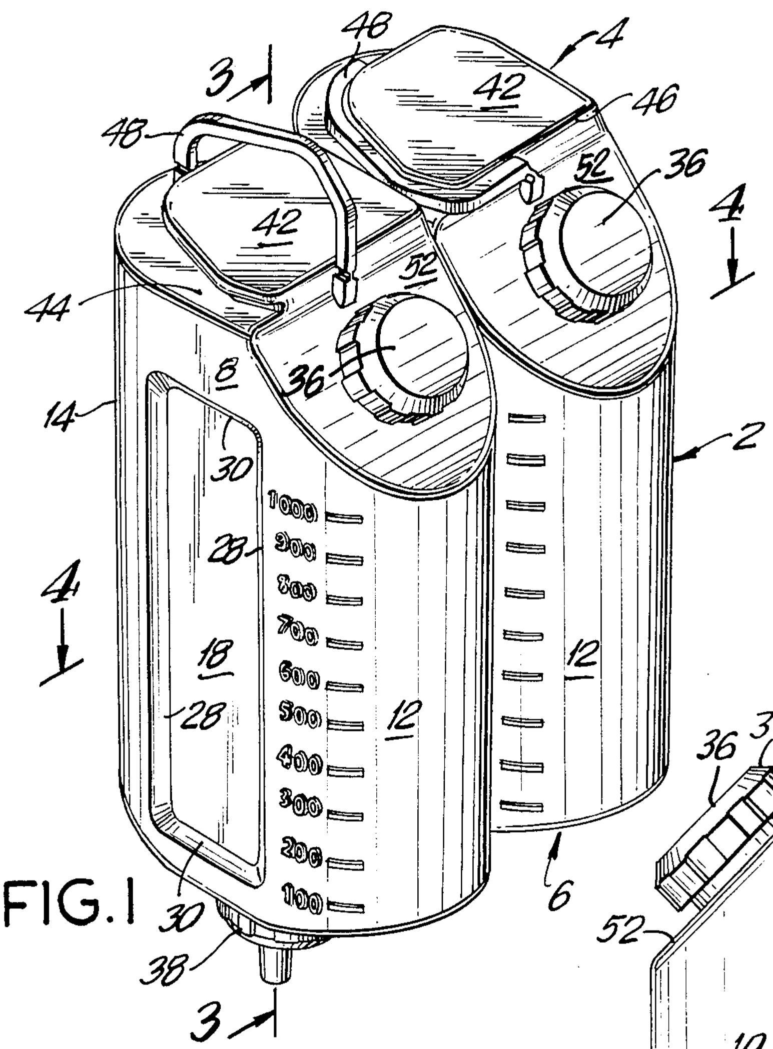
FIG. 1 is a plan elevation view showing two of the enteral containers in nesting relationship, one having the handle up and the other having the handle down.

Referring to the drawings, there is shown a generally rectangular container 2 having an upper end 4 and a lower end 6. One side 8 of the container (referred to for convenience as the front) is marked with indicia to indicate the quantity of liquid nourishment within the container. The other side 10 of the enteral feeding container (referred to for convenience as the rear) is also marked with indicia showing the volume of liquid nourishment within the container. The volume indicating indicia on the rear surface is upside down with respect to the indicia on the front surface. As will be explained this is necessary when the liquid nourishment is supplied to the container when it is in the upside down position.

The front 8 and rear 10 surfaces are joined by the curved surfaces 12 and 14 which conveniently fit into the hand of the attendant or nurse for ease in handling.

In accordance with this invention means is provided for permitting space saving, efficient storage of the enteral feeding containers. As embodied, this means includes on each enteral feeding container a lengthwise extending recess on one longitudinally extending side of the container and a lengthwise extending projection on the other longitudinally extending side of the container. (See e.g. FIGS. 1, 2 and 4)

It will be understood that each container is formed identically so that a plurality of them can be nested together in side-by-side or stacked relationship for shipping, for example, from the manufacturer to another facility.

Figure 3:
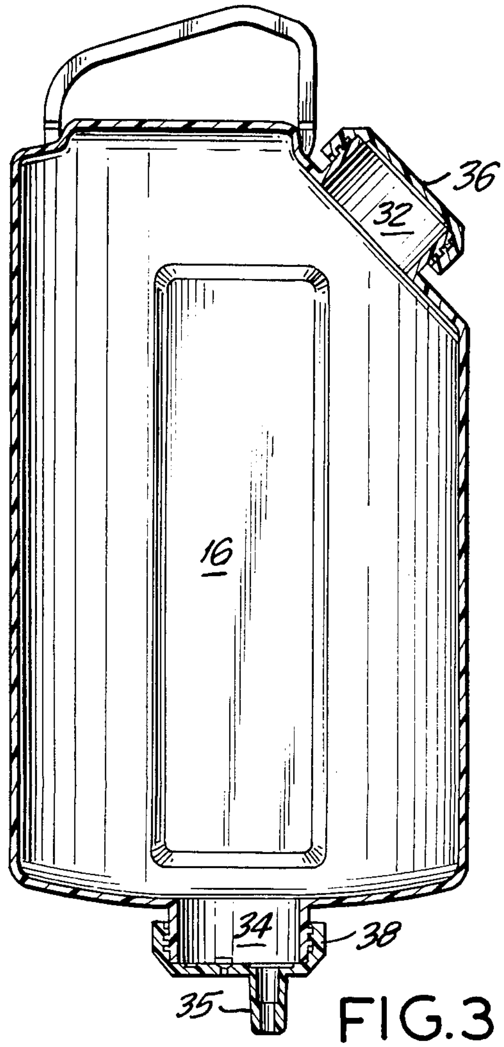
FIG. 3 is a sectional view of the enteral feeding container in accordance with this invention taken along line 3—3 of FIG. 1.

Referring to the drawings, the projection 16 and the recess 18 extend substantially along the entire longitudinal length of their respective sides. As can be seen, the projection and recess occupy virtually the entire width of the flat portion of their respective sides. Referring to the drawings, e.g. Fig. 3, the projection consists of an outer substantially flat surfae 20 and longitudinally extending outwardly inclined surfaces 22 and transversely extending inclined surfaces 24 which joins the surfaces 22. The recess 18 consists of an inwardly positioned substantially flat surface 26 and an inclined longitudinally inwardly extending side surfaces 28. The recess terminates at each end with the transverse inclined surfaces 30 which joins the surfaces 28.

Figure 2:
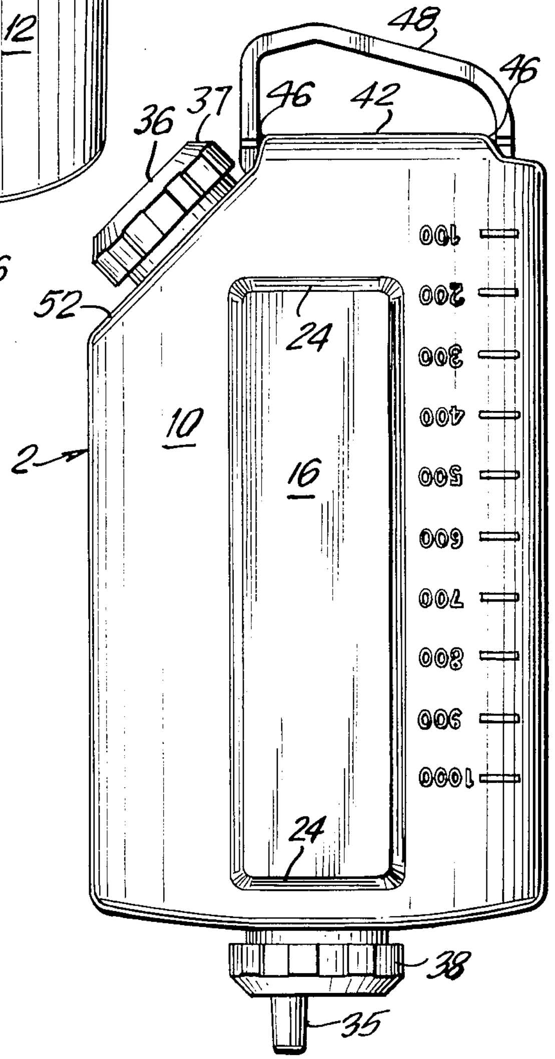
FIG. 2 is a rear view of the enteral feeding container in accordance with this invention.
Figure 4:
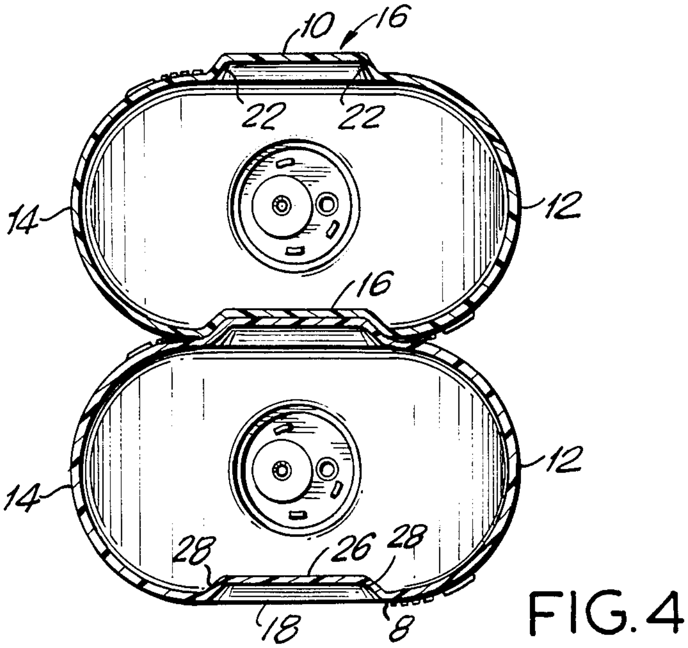
FIG. 4 is a sectional view of the enteral feeding container in accordance with this invention taken along line 4—4 of FIG. 1.

As is apparent the length and width of the projections 16 are somewhat less than the length and width of the recesses 18 so that the projections can fit within the recesses in nesting or mating relationship as illustrated in FIGS. 1 and 4. Because of the mating or nesting relationship, the enteral feeding containers can be positioned in side-by-side or stacked relationship for convenience in shipping and storage.

In accordance with this invention, means is provided to permit liquid nourishment to be filled to the container at the patient's bedside or at the formulary.

Referring to the drawings, there is an upper spout opening 32 and a lower spout opening 34. Each spout opening is adapted to be closed by a cap 36 and 38, respectively adapted to be threaded to the opening. The upper end of the container has a substantially flat end surface 42 which is raised somewhat from the remainder of the container to form a shelf 44. Hingedly attached to the ends 46 of the raised flat surface is a handle 48 adapted in one position to straddle the raised flat surface 42 (See FIGS. 1 and 2). When the handle is in the upright position it can be placed on a hook or the like for feeding liquid nourishment to the patient by gravity through the bottom opening 34 which may be provided with a discharge nozzle or nipple 35. When in this upright position the cap 36 can be removed and additional liquid nourishment supplied to the container.

Figure 5:
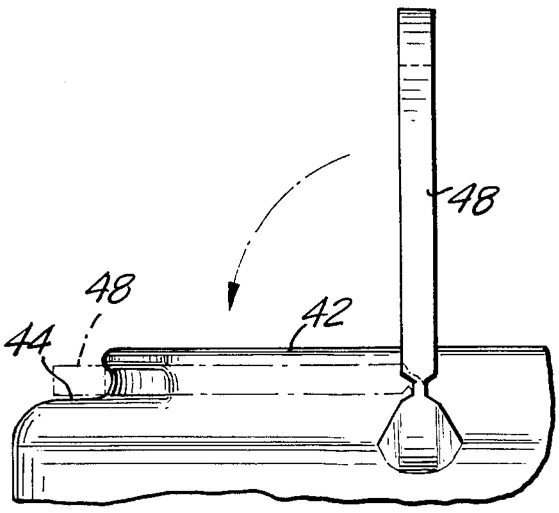
FIG. 5 is a partial view showing the hinged handle for the enteral feeding container of this invention.

The handle 48 has a second position shown in dot-dash lines in FIG. 5 and in full line position in FIG. 1. When in this position the handle 48 rests on the shelf 44 so that the container can be supported by the flat surface 42 in the upright (upside down) position.

The container adjacent its upper end includes a beveled or slanted surface 52 through which the opening 32 extends. The slanted surface 52 facilitates filling of the device. A feature of this invention is that the cap member 36 for the opening 32 stabilizes the enteral feeding container when in the upside down upright position. The cap 36 includes a beveled surface 37 which will be in the horizontal position when the cap is in its operative position. Thus, with the handle 48 in its out-of-the-way position on shelf 44 and the container in the upside down position, the beveled surface 37 will be in the horizontal position to stabilize the container. When in this upside down position the cap 38 can be removed and liquid nourishment supplied to the container. This arrangement is particularly advantageous when it is necessary that a special nourishment formulation be prepared in the formulary and fed into the container.

It will also be noted that when the handle 48 is in the out-of-the-way position that adjacent container can be placed in end-to-end relationship in a space saving manner for storage and shipping. When in this position, the flat upper surfaces 42 are in face-to-face relationship.

What is claimed is:

1. An enteral feeding device comprising:
   a. a rigid plastic substantially rectangular container adapted to contain a supply of liquid nourishment, said container including a substantially flat front wall and a substantially flat rear wall.
   b. curved walls joining the front and rear walls,
   c. a projection extending from one of said front and rear walls, said projection having a length substantially equal to the length of the container and a width substantially equal to the width of the flat portion of the wall;
   d. a recess on the other of said front and rear walls, said recess having a length substantially equal to the length of the container and a width substantially equal to the width of the flat portion of the wall;
   e. said projection and said recess being dimensioned so that the projection on said container can nest in the recess of another container in side-by-side relationship, and
   f. an opening with a spout at one end of the container and another opening with a spout at the other end of the container, said openings being adapted to permit the flow of liquid nourishment therethrough.

2. An enteral feeding device as defined in claim 1 wherein one end of the container has a raised surface which is substantially flat and forms a shelf immediately adjacent the top of the container.

3. An enteral feeding device as defined in claim 2 having a handle hinged to the container to straddle the raised surface in one first position and which rests on the shelf in another second position.

4. An enteral device as defined in claim 3 having an inclined surface extending from one of the curved surfaces to said raised surface with one of said openings extending through said inclined surface.

5. An enteral feeding device as defined in claim 4 having a cap in assembled relationship with at least one of said spout, said cap having a beveled surface which cooperates with said flat surface to support said container in an upright upside down position when said handle is in said second position so that liquid nourishment can be filled to said container when in the upside down position.

6. An enteral feeding device as defined in claim 5 having indicia markings on the front and rear of said container so that the volume of liquid nourishment can be visually observed whether the container is in its normal upright position or in the upside down position.

7. An enteral feeding device adapted to store and supply liquid nourishment comprising;

(a) a substantially rigid plastic container adapted to contain a supply of liquid nourishment, said container including a front wall and a rear wall, (b) side walls joining said front and rear walls, (c) a first opening at one end of said container and a second opening at the other end of said container, each of said openings adapted to be closed by cap means, (d) means formed on said one end of said container permitting said container to be positioned vertically in one direction to permit the supplying of liquid nourishement to the container through said second opening, and (e) means formed on said one end of said container permitting said container to hang vertically in the other direction permitting gravity feeding of liquid nourishment through said second opening and the supplying of liquid nourishment through said first opening to said container, (f) said means for permitting vertical positioning of said container in said one direction including a raised, substantially flat surface formed at said one end of said container which forms a shelf adjacent the top of said container, (g) said means for permitting the vertical hanging of said container in said other direction including a handle hinged to the container to straddle said raised surface in a first position so that the device can hang vertically and which is adjacent said shelf in a second position to permit said container to be positioned in said one direction.

8. An enteral feeding device as defined in claim 7 wherein said cap means includes a cap member on said first opening positioned and shaped so that it assists in cooperating with said raised flat surface to permit vertical standing of said container in said one direction on said flat surface.

9. An enteral feeding device adapted to store and supply liquid nourishment comprising;

(a) a substantially rigid plastic container adapted to contain a supply of liquid nourishment, said container including a front wall and a rear wall, (b) side walls joining said front and rear walls, (c) a first opening at one end of said container and a second opening at the other end of said container, each of said openings adapted to be closed by cap means.

(d) means formed on said one end of said container permitting said container to be positioned vertically in one direction to permit the supplying of liquid nourishement to the container through said second opening, (e) mean formed on said one end of said container permitting said container to hang vertically in the other direction permitting gravity feeding of liquid nourishment through said second opening and the supplying of liquid nourishment through said first opening to said container, (f) a projection extending from one of said front and rear walls, said projection extending along the length of said container, and (g) a recess on the other of said front and rear walls lengthwise of said container and dimensioned so as to receive a projection on another container like said first named projection in nesting relationship.

10. An enteral feeding device as defined in claim 9 having indicia markings on the front and rear of said container so that the volume of liquid nourishment can be visually observed whether the container is in said first position or in said second position.

* * * * *